US00PP10443P

United States Patent [19]

Wiles

[11] Patent Number: Plant 10,443

[45] Date of Patent: Jun. 9, 1998

[54] VARIETY OF IVY GERANIUM NAMED 'GLOBAL RICH RED'

[75] Inventor: Linda S. Wiles, Scottdale, Pa.

[73] Assignee: Oglevee, Ltd., Connellsville, Pa.

[21] Appl. No.: 665,506

[22] Filed: Jun. 18, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,271 7/1990 Guillou et al. ..... Plt./87.12
P.P. 7,358 10/1990 Guillou et al. ..... Plt./87.12
P.P. 8,100 1/1993 Heidgen ..... Plt./87.12
P.P. 8,305 7/1993 Schumann ..... Plt./87.12
P.P. 8,306 7/1993 Schumann ..... Plt./87.12

*Primary Examiner*—Howard J. Locker
*Assistant Examiner*—Kent L. Bell
*Attorney, Agent, or Firm*—Webb Ziesenheim Bruening Logsdon Orkin & Hanson, P.C.

[57] ABSTRACT

A new and distinct variety of ivy geranium adding a true red color to the ivy geranium group. The new variety is similar in color to Simone and has a similar habit to Nicole. The new variety is non-shattering and has a deep red color on medium green foliage.

1 Drawing Sheet

BACKGROUND OF THE NEW PLANT

The present invention comprises a new and distinct cultivar of *Pelargonium×peltatum* known by the varietal name 'Global Rich Red'. The new variety was discovered in a selective breeding program at Oglevee, Ltd. by Linda S. Wiles. The new variety is a selection from a seedling cross from 'Nicole', the seed parent,×'Simone' the pollen parent, (U.S. Plant Pat. Nos. 7,358 and 7,271, respectively).

The new cultivar was discovered in 1993 at 152 oglevee Lane, Connellsville, Pa., and was first asexually reproduced by cuttings on Jan. 25, 1994 at Connellsville, Pa. It has been found to retain its distinct characteristics through successive propagations.

The new cultivar is similar in color to the variety 'Simone' and is similar in habit to the variety 'Nicole'. The new cultivar is less prone to shatter than either parent.

The new cultivar, when grown in a glass greenhouse in Connellsville, Pa., using full light, 60° F. night temperature, 68° F. day temperature, and grown in a soilless media with constant fertilizer of 200–250 parts per million nitrogen and potassium, has a response time from a rooted cutting to a flowering plant in 10 cm. pot of six weeks.

DESCRIPTION OF THE DRAWING

The accompanying drawing illustrates the new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee, Ltd. in Connellsville, Pa. The plants were started as rooted cuttings which were potted and then flowered six weeks later. The plant histories were taken of plants blossomed under full light in a greenhouse and color readings were taken indoors under 200–220 foot candles of cool white fluorescent light. Color references are primarily to the R.H.S. Colour Chart of The Royal Horticultural Society of London.

The Plant

Classification:
- *Botanical.*—*Pelargonium×peltatum.*
- *Commercial.*—Ivy geranium named 'Global Rich Red'.

Form: Cascading mound.
Height: 19 cm. from media.
Growth: Free-branching, upright mound with cascading side growth.
Strength: Does not need artificial support.
Foliage: Stalked leaf attachment; faint zone present.
Leaves:
- *Size.*—7.5 to 8.3 cm. fully extended.
- *Shape.*—Reniform, cordate base.
- *Margin.*—Pedately lobed.
- *Texture.*—Smooth/slippery, yet leathery.
- *Color.*—Top: Green Group 137A; Bottom: Green Group 137D; Zone (not prominent): Brown Group 200A (when visible).
- *Ribs and veins.*—Venation: Palmate. Color: Green Group 143A.

Petioles:
- *Length.*—4.6 to 6.5 cm.
- *Color.*—Green Group 143A.

Stem:
- *Color.*—Green Group 143A.

Internodes: 3.5 to 4.5 cm. in length.

The Bud

Shape: Elliptical cluster.
Size: 4.5 cm. (just breaking color).
Color: Red-purple group 61B.

Inflorescence

Blooming habit: Continuous, free and early flowering.
Borne: Florets on pedicel; pedicel on peduncle at 11 to 12.5 cm. above foliage.
Closed florets: Bud size: 1.4 to 2 cm. in height at cracking color stage.
- *Number of florets per inflorescence.*—7 to 10.
- *Size.*—Fully Open Bloom: 8 to 10 cm.

Open florets:

*Form.*—Lower petals flatten, inner petal form cup; becomes flatter as it ages.

*Color.*—Top: Overall color is Red Group 53B — inner petals have white base which forms a blushed appearance near center of floret, outer edge of petals fade to light pink as they near the base giving a streaked appearance. Bottom: Red Group 52A (eye same as the top of petal). Outer edge: Red Group 53B. Inner group: Red Group 53A. Eye: Prominent dark veining at darkest, Greyed-purple Group 187A with highlights around veins being Red Group 55A.

Petals: About 12.

Size: 4.5 to 5 cm. open floret.

Texture and appearance: Rich velvety; satin look of deep red on medium green foliage.

Petaloids:

*Quantity.*—2 to 3.

*Shape.*—Irregular, twisted, some petal-like; some with anther attached.

*Color.*—Top Red group 53B; Bottom: Red group 52A.

Pedicel:

*Length.*—2 to 3 cm.

*Color.*—Green group 143A.

Peduncle:

*Length.*—16 to 17 cm.

*Color.*—Green Group 143A.

Disease resistance: Not known.

Lasting quality: Less prone to shatter or falling apart than 'Nicole' and 'Simone'. Inflorescence stays open 7 to 10 days before shattering occurs (3 to 5 days longer than 'Simone'.

Reproductive Organs

Stamens:

*Anthers.*—3 mm. in length.

*Filaments.*—1 to 1.2 cm. in length, white to very pale pink in color.

*Pollen.*—Golden Brown.

Pistils:

*Number.*—1;5 parted.

*Length.*—3 to 4 mm.

*Stigma.*—Deep red-purple in color; same as dark veins on eye.

*Style.*—Length: 3 mm. Color: Green-White Group 157C.

*Ovaries.*—Color: Green; superior; pubescent. Length: 6 to 7 mm.

Fruit: None observed.

GENERAL CHARACTERISTICS

A new geranium plant that provides a true red color to the ivy geranium group. Cutting production, rooting time and finishing are all excellent.

I claim:

1. A new and distinct variety of ivy geranium plant as shown and described herein and characterized by a deep red color on a medium green foliage, and being non-shattering.

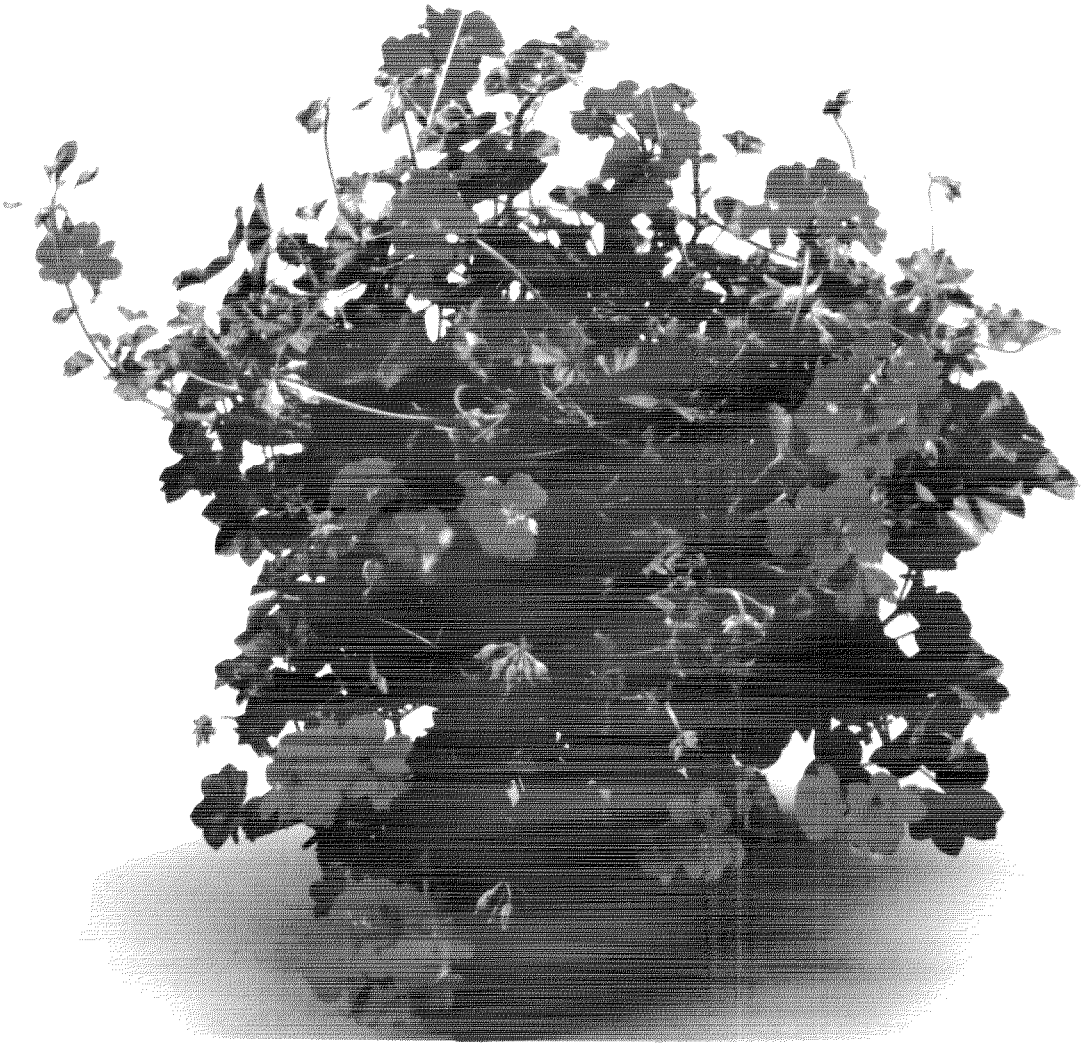

* * * * *